US012485220B2

(12) United States Patent
Marggi et al.

(10) Patent No.: US 12,485,220 B2
(45) Date of Patent: Dec. 2, 2025

(54) INFUSION SET FOR AN INFUSION DEVICE

(71) Applicant: Ypsomed AG, Burgdorf (CH)

(72) Inventors: Rolf Marggi, Bern (CH); Christoph Renggli, Grenchen (CH); Andreas Zurflüh, Hasle-Rüegsau (CH)

(73) Assignee: Ypsomed AG, Burgdorf (CH)

( * ) Notice: Subject to any disclaimer, the term of this patent is extended or adjusted under 35 U.S.C. 154(b) by 1234 days.

(21) Appl. No.: 17/236,475

(22) Filed: Apr. 21, 2021

(65) Prior Publication Data

US 2021/0236724 A1 Aug. 5, 2021

Related U.S. Application Data

(63) Continuation of application No. PCT/IB2019/058636, filed on Oct. 10, 2019.

(30) Foreign Application Priority Data

Oct. 23, 2018 (EP) .................................... 18201927

(51) Int. Cl.
*A61M 5/162* (2006.01)

(52) U.S. Cl.
CPC ......... *A61M 5/162* (2013.01); *A61M 2205/14* (2013.01)

(58) Field of Classification Search
CPC .............. A61M 5/162; A61M 2205/14; A61M 2005/1583; A61M 2005/1585;
(Continued)

(56) References Cited

U.S. PATENT DOCUMENTS

| | | | | |
|---|---|---|---|---|
| 6,355,021 B1 * | 3/2002 | Nielsen | ............. | A61M 25/0631 604/93.01 |
| 6,736,797 B1 * | 5/2004 | Larsen | .................. | A61M 5/158 604/533 |

(Continued)

FOREIGN PATENT DOCUMENTS

| | | |
|---|---|---|
| EP | 1984044 B1 | 2/2011 |
| EP | 1694385 B1 | 10/2016 |

(Continued)

OTHER PUBLICATIONS

International Preliminary Report on Patentablity received for International Application No. PCT/IB2019/058636, mailed on Apr. 27, 2021, 8 pages.

*Primary Examiner* — Theodore J Stigell
(74) *Attorney, Agent, or Firm* — Dorsey & Whitney LLP

(57) ABSTRACT

An infusion set includes a base having a cannula for delivering a liquid medicament on a distal side for placing on a patient and a projection and recess and/or an annular groove on a proximal side. A connector for connection to an infusion device includes a protrusion on a distal side. The base and the connector are rotatably connectable to each other. The protrusion of the connector may be engaged with the projection and recess of the base such that, upon relative rotation between the connector and base, an acoustic and/or tactile signal indicates that the connector is connected incorrectly to the base; and/or the protrusion of the connector may be brought into engagement with the annular groove of the base such that the connector is rotatable relative to the base without causing noise and/or a tactile signal to indicate that the connector is connected correctly to the base.

20 Claims, 11 Drawing Sheets

(58) Field of Classification Search
CPC ...... A61M 2005/1586; A61M 2205/44; A61M 25/02; A61M 5/158; A61M 2205/58–583; A61M 2039/1044
See application file for complete search history.

(56) References Cited

U.S. PATENT DOCUMENTS

| | | | | |
|---|---|---|---|---|
| 7,892,216 | B2 * | 2/2011 | Fangrow, Jr. | A61M 25/0606 604/288.02 |
| 8,152,769 | B2 | 4/2012 | Douglas et al. | |
| 2005/0020972 | A1 * | 1/2005 | Horisberger | A61M 5/158 604/93.01 |
| 2005/0101910 | A1 * | 5/2005 | Bowman | A61M 25/02 604/93.01 |
| 2017/0290533 | A1 | 10/2017 | Antonio et al. | |

FOREIGN PATENT DOCUMENTS

| | | | |
|---|---|---|---|
| EP | 3643346 | A1 | 4/2020 |
| WO | 2007140631 | A1 | 12/2007 |
| WO | 2020084374 | A1 | 4/2020 |

* cited by examiner

INFUSION SET FOR AN INFUSION DEVICE

CROSS-REFERENCE TO RELATED APPLICATIONS

This application claims priority to International Patent Application No. PCT/IB2019/058636, filed Oct. 10, 2019, entitled "INFUSION SET FOR AN INFUSION DEVICE," which in turn claims priority to European Application No. 18201927.3, filed Oct. 23, 2018, entitled "INFUSION SET FOR AN INFUSION DEVICE", each of which is incorporated by reference herein, in its entirety and for all purposes.

TECHNICAL FIELD

The present disclosure relates to an infusion set for an infusion device. Infusion sets are used to deliver a liquid product, such as a liquid medicament, from an infusion device into the body of a patient.

BACKGROUND

The term "medicament" here encompasses any flowable medical formulation which is suitable for controlled administration by a means, such as a cannula or a hollow needle, for example a formulation comprising a liquid, a solution, a gel or a fine suspension, which contains one or more medicinal active ingredients. Medicament may be a single agent composition or a premixed or co-formulated multiple agent composition from a single container. Drug includes drugs such as peptides (e.g. insulins, drugs containing insulin, GLP-1 containing and derived or analogous preparations), proteins and hormones, biologically obtained or active ingredients, active ingredients based on hormones or genes, nutritional formulations, enzymes and other substances both in solid (suspended) or liquid form but also polysaccharides, vaccines, DNA or RNA or oligonucleotides, antibodies or parts of antibodies as well as suitable basic, auxiliary and carrier substances.

In the case of patients who have a regular need for a liquid medicament, the required amount of medicament may be supplied to the body in liquid form by means of a cannula arranged in the subcutaneous tissue over a longer period of time. For this purpose, an infusion set with a cannula made of a soft material or a rigid material is attached to the patient's skin in such a way that the cannula penetrates through the skin into the subcutaneous tissue. The required amount of medication is administered in liquid form from an infusion device, such as from an infusion pump, for instance from an automatic infusion pump via a supply line to the patient, the cannula in the infusion set supplying the patient with the liquid medication.

Infusion sets are known from the prior art. The documents U.S. Pat. No. 8,152,769B2, EP1694385B1 and EP1984044B1 disclose infusion sets which have a base part with a cannula, the cannula serving to penetrate through the skin into the subcutaneous tissue in order to administer a liquid medicament to a patient. Furthermore, the infusion sets have a connector part to which a supply line, such as a tube, is attached. The supply line may be connected to an infusion device, such as an infusion pump. Thus, the liquid medicament may be administered to the patient by the infusion device through the infusion set. The connector part and the base part may be rotatable relative to one another, for instance may be rotatable relative to one another through any desired angle. With this arrangement, the wearing comfort may be improved. The disadvantage of these infusion sets is that the handling and/or the operation of these infusion sets are made more difficult, since operating errors are possible.

SUMMARY

It is an object of the present disclosure to provide an alternative infusion set, the handling and/or operation of the infusion set being facilitated in order to prevent incorrect operation.

In the infusion sets according to the present disclosure, the distal direction means the side to which an adhesive layer may be attached in order to attach the infusion set to the skin of a patient. In the case of the infusion set according to the present disclosure, the proximal direction means the side that may be connected to an infusion device.

The infusion set according to the present disclosure may be attached to an infusion device, such as an infusion pump, including an automatic infusion pump. Infusion devices may be used for the continuous administration of infusions, such as drugs in liquid form. The infusion device may be a reusable infusion device, a new container pre-filled with a liquid medicament may be insertable into the reusable infusion device. On the other hand, the infusion device may be a single-use infusion device, and the infusion device may be discarded when a container pre-filled with a liquid medicament is empty. The infusion set may include a base part for attachment to the skin of a patient, where the base part includes a proximal side and a distal side. Furthermore, the base part may include a cannula for feeding the liquid medicament into the patient's body. The cannula may be provided on the distal side of the base part. Furthermore, the infusion set may include a connector part with a supply line, such as a tube. The connector part may have a proximal side and a distal side. The supply line may be used for connection to the infusion device. Furthermore, the supply line may be used to connect to the base part such as by a piercing cannula in order to form a fluid path between the connector part and the base part. Furthermore, the infusion set can comprise a cap part for holding the infusion set by the patient or by an insertion device or insertion aid, wherein the cap part can have a distal side and a proximal side. The infusion set may be configured, in a first embodiment, with a soft cannula, where the cannula may be formed of a soft material, such as a polymer, or, in a second embodiment, with a rigid cannula, the cannula being formed from steel or from an alternative rigid material.

In the first embodiment of the infusion set, the cap part of the infusion set may have a stiff or rigid needle, where the needle is formed of steel or of an alternative rigid material. The cap part may become or may be detachably connected to the base part. The connection may be configured as a snap (or snap-action) connection. Alternative connections may also be provided. The cap part may be connected, for instance snapped, to the base part in such a way that the rigid needle may be arranged concentrically in a soft cannula of the base part. The soft cannula may be used to deliver a liquid medicament into the body of a patient. The cap part may be arranged on the proximal side of the base part. The concentric arrangement of the soft cannula and the rigid needle may serve to guide the soft cannula when the soft cannula of the base part is pierced into the patient's skin. The distal tip of the rigid needle may protrude over the distal end of the soft cannula. Furthermore, an adhesive layer may be arranged on the distal side of the base part. The adhesive layer may be used to attach the infusion set to the patient's skin. In order to attach the infusion set to the patient's skin, the base part connected to the cap part, for instance snapped into place, may be adhered to the patient's skin using adhesive layers, a protective film being removed from one side of the adhesive layer beforehand. The soft cannula with the fixed, rigid needle arranged therein may penetrate through the patient's skin and into the patient's subcutaneous tissue. To connect the infusion set to an infusion device, the cap part with the rigid needle may first be removed from the base part and a connector part, which may comprise a supply line, such as a tube and an adapter, may be attached to the base part of the infusion set. The connection between the base part and the connector part may be configured as a snap connection. Alternative connections may be provided. A first end of the feed line may be welded, bonded and/or glued to the adapter. A second end of the feed line may be welded, bonded and/or glued to the connector part. For instance, the feed line may be attached to the adapter and/or to the connector part using an adhesive, such as an adhesive that may cure by exposure to UV light. This means that solvents, which are used during welding, gluing, or bonding, may be avoided. The use of solvent may be undesirable because a solvent could enter the fluid path and thus contaminate the liquid medicament being dispensed. The adapter of the connector part may be detachably attached to a corresponding connecting element of the infusion device. The adapter of the connector part may be connected to the injection device by means of a bayonet lock, Luer lock or another lock. A fluid path may thus be established from the infusion device via the infusion set to the patient.

The adapter of the connector part may include a valve. The valve may be configured in such a way that the valve may open and close. The valve may be configured as a check valve, such as a diaphragm check valve. The valve may comprise a liquid inlet and a liquid outlet for the liquid medicament.

The valve may also be configured in such a way that it may open when the pressure of the liquid medicament in the flow inlet exceeds a previously determined threshold value. An uncontrolled release of the liquid medicament may thereby be prevented.

The valve may also be configured in such a way that the liquid medicament may only flow in one direction from the liquid inlet to the liquid outlet. This may prevent the liquid medicament to be dispensed from flowing back.

In the second embodiment of the infusion set, the infusion set may include a cap part. The base part may include a rigid cannula. The rigid cannula may be used to deliver a liquid medicament into the body of a patient. The cap part may become or may be detachably connected to the base part. The connection may be configured as a snap connection. Alternative connections may be provided. The base part may be arranged at the distal end of the cap part. On the distal side of the base part, an adhesive layer may be provided for attaching the infusion set to the patient's skin. In order to attach the infusion set to the patient's skin, the base part connected to the cap part, e.g., snapped into place, may be attached to the patient's skin by means of adhesive layers, a protective film being removed beforehand from an adhesive side of the adhesive layer. The rigid cannula of the base part may penetrate the subcutaneous tissue of the patient. The cap part may then be removed from the base part in order to releasably connect a connector part to the base part. The connector part may include a supply line, such as a tube and an adapter, in order to releasably connect the infusion set to an infusion connection. The connection between the base part and the connector part may be configured as a snap connection. Alternative connections may be provided. The supply line may be welded and/or attached (e.g., glued) to the adapter with a first end and welded and/or attached to the connector part with a second end. For instance, the feed line may be attached to the adapter and/or to the connector part using an adhesive that may cure by exposure to UV light. This means that solvents, which are used during welding, gluing, or bonding, may be avoided. The use of solvent may be undesirable because a solvent could enter the fluid path and thus contaminate the liquid medicament being dispensed. The adapter of the connector part may be detachably attached to a corresponding connecting element of the infusion device.

The adapter of the connector part may be connected to the injection device by means of a bayonet lock, Luer lock or another lock. A fluid path may thus be established from the infusion device via the infusion set to the patient.

The adapter of the connector part may include a valve. The valve may be configured in such a way that the valve may open and close. The valve may be configured as a check valve, such as a diaphragm check valve. The valve may include a liquid inlet and a liquid outlet for the liquid medicament.

The valve may also be configured in such a way that it may open when the pressure of the liquid medicament in the flow inlet exceeds a previously determined threshold value. An uncontrolled release of the liquid medicament may thereby be prevented.

The valve may also be configured in such a way that the liquid medicament may only flow in one direction from the liquid inlet to the liquid outlet. This may prevent the liquid medicament to be dispensed from flowing back.

The first and the second embodiment of the infusion set may include a detachable protective element. The protective element may serve to protect against puncture injuries by the rigid cannula or by the rigid needle of the corresponding infusion set. The protective element may be configured in the form of a sleeve. Alternative configurations of the protective element may be provided. One or more longitudinal ribs may be provided on a jacket outer surface of the protective element for better gripping of the protective element. Thus, before the infusion set is attached to the patient's skin, the patient may simply remove the protective element from the base part and, after removing the infusion set from the patient's skin, simply put the protective element back on over the rigid cannula of the base part or over the rigid needle of the cap part, whereby the patient may thus be protected from puncture injuries. The protective element may be releasably connected to the base part and/or the cap part with a force fit and/or with a form fit in order to protect the patient from a puncture injury.

The base part of the first and second embodiment of the infusion set may be flat. To guide and/or position the base part relative to the cap part and/or to the connector part, a base cylinder may be provided on the proximal side of the base part of the first and second embodiment of the infusion set. The base cylinder may protrude from the proximal side of the base part in the proximal direction. The base cylinder may be cylindrical. The base cylinder may be arranged concentrically to the soft cannula or to the rigid cannula of the corresponding infusion set.

Furthermore, an opening may be provided in the base part of the first and the second embodiment of the infusion set. The opening may be configured as a blind hole. The opening may be arranged on the distal side of the base part and may be provided in the base cylinder. The opening may be arranged concentrically to the soft cannula or to the rigid cannula of the corresponding infusion set. The opening may be configured in such a way that the opening may receive the protective element, such as by a force fit. Alternatively, the opening and the protective element may be configured such that the protective element may be received in the opening in a form-fitting manner.

Furthermore, a cannula cylinder may be provided on the distal side of the base part on the base part of the first and the second embodiments of the infusion set. The cannula cylinder may be cylindrical. The cannula cylinder may be provided in the opening of the base part. The cannula cylinder may protrude from the distal side of the base part in the distal direction. The soft or the stiff cannula may be fastened in the corresponding cannula cylinder, for instance in a passage provided in the cannula cylinder, and may protrude from the corresponding cannula cylinder in the distal direction in order to deliver the liquid medicament to the patient.

Before the corresponding infusion set is attached to the patient's skin, the protective element may be detachably connected to the base part with a force fit so that the protective element may protect the patient from a puncture injury caused by the rigid cannula or the rigid needle of the corresponding infusion set. The protective element may be releasably pressed or pressed into the opening of the base part in such a way that the protective element is subjected to compression. The compressive force on the protective element may lead to less damage, e.g., cracks, to the protective element than if the protective element is arranged on the cannula cylinder of the base part and is thus subjected to tensile stress. Furthermore, the diameter of the protective element may be larger so that the patient may better grip the protective element in order to remove the protective element from the base part and/or place it on the base part. This arrangement may also reduce the pressure on the cannula cylinder so that the cannula cylinder is not damaged, for example by cracks or dents.

Alternatively, the base part may have one or more recesses, where one or more pin-shaped elements provided on the protective element may be releasably pressed or pressed into the recess or the plurality of recesses in order to protect the patient from puncture injuries. Alternatively, the recess or the plurality of recesses and the pin-shaped element or the plurality of pin-shaped elements may be configured in such a way that the recess or the plurality of recesses may receive the pin-shaped element or the plurality of pin-shaped elements in a form-fitting manner.

The cap part of the first and the second embodiment of the infusion set may be configured in the shape of a cap. A cap cylinder may be provided on the inside of the shell of the cap part. The cap cylinder may be cylindrical. The cap cylinder may be formed in one piece or in several pieces. The cap cylinder may be configured as a hollow cylinder. The cap cylinder may extend from the inside of the jacket in the distal direction. The cap cylinder may be arranged on the cap part in such a way that when the cap part is connected, such as snapped, to the base part, the cap cylinder may be arranged concentrically to the base cylinder of the base part. When the cap part is connected to the base part, such as snapped into place, or is removed from the base part, the base cylinder may be in a guiding engagement with the cap cylinder, such as a sliding engagement. The cap cylinder of the cap part may surround the base cylinder of the base part. The cap part may be arranged such that it is axially movable with respect to the base part when it is connected, e.g., snapped onto the base part and/or released from the base part.

The connector part of the first and the second embodiment of the infusion set may be configured in the shape of a cap. Furthermore, a connector cylinder may be provided on the inside of the jacket of the connector part. The connector cylinder may be cylindrical. The connector cylinder may extend from the inside of the jacket in the distal direction. The connector cylinder may be arranged on the connector part in such a way that when the connector part is connected, for instance snapped, to the base part, the connector cylinder may be arranged concentrically to the cannula cylinder of the base part. The connector cylinder of the connector part may be arranged outside the base cylinder of the base part. The connector cylinder may be formed in one piece or in several pieces. The connector cylinder may be configured as a hollow cylinder, where a piercing cannula may be arranged concentrically and/or coaxially to the connector cylinder in the interior of the connector cylinder. The piercing cannula may be configured as a separate part, such as a separate steel cannula or as part of the connector part. The piercing cannula may be connected to the supply line, such as to the tube. When the connector part is connected to the base part, such as snapped into place, or is removed from the base part, the base cylinder may be in a guide engagement, such as a sliding engagement, with the connector cylinder. If the connector cylinder is arranged concentrically to the base cylinder, the connector part may rotate relative to the base part, and may rotate through any desired angle. The connector part and the base part may be arranged to be axially movable and rotatable relative to one another, such as rotatable through any desired angle.

In the first embodiment of the infusion set, the rigid cannula may be inserted with the correct length in the base part, such as in the cannula cylinder, such as in the passage of the cannula cylinder of the base part, and an adhesive may be used to fasten the rigid cannula in the base part outside the fluid path, such as between the rigid cannula and the cannula cylinder of the base part. Thus, contamination of the liquid medicament to be dispensed by the adhesive may be avoided. An adhesive may be used which may cure by exposure to UV light in order to dispense with solvents. Alternative fastening means for fastening the rigid cannula to the base part may be provided.

In the second embodiment of the infusion set, the soft cannula with the correct length may be inserted into the base part, such as into the cannula cylinder of the base part, or it may be cut to the correct length in the inserted state. A connecting part may be used for the connection, such as for the firm connection of the soft cannula in the base part. The connecting part may be tubular at the distal end and funnel-shaped at the proximal end. Other forms of design of the connecting part may be provided. The connecting part may be formed from a rigid material, such as from steel. The connecting part may be called an "eyelet". The "eyelet" may serve to guide the rigid needle which may be arranged on the cap part. In order to be able to insert the soft cannula into the base part, the soft cannula may first be attached or pushed onto or over the "eyelet", such as over the distal part of the "eyelet". The soft cannula may be positively connected to the "eyelet", for instance it may be pressed. The "eyelet" connected to the soft cannula may then be pressed into the passage provided on the cannula cylinder. The "eyelet" connected to the soft cannula may be positively connected to the base part. The proximal part of the "eyelet" may be arranged on the proximal side of the cannula cylinder and the distal part of the "eyelet" may be arranged on the distal side of the cannula cylinder.

Furthermore, a septum may be arranged in the cannula cylinder of the first and second embodiment of the infusion set. In the first embodiment of the infusion set, the septum may be arranged at the proximal end of the rigid cannula for closing the passage of the cannula cylinder. In the second embodiment of the infusion set, the septum may be provided at the proximal end of the "eyelet" to close the passage of the cannula cylinder. The septum may serve to close the base part to prevent undesired fluid flow. The piercing cannula of the connector part may pierce the septum of the base part, for instance if the connector part is connected to the base part, such as snapped onto it, in order to form a fluid connection.

The supply line, such as the tube of the first and second embodiment of the infusion set, may include an outer material and an inner material. The outer material may include a polyurethane (PU), such as Elastollan® 1185 A 10FC. The inner material may include a high density polyethylene (HDPE), such as SABIC® HDPE B5429 or a polypropylene (PP), such as Bormed™ SC820CF-11. An alternative outer and/or inner material may be provided.

In one embodiment of the feed line, such as the tube, the feed line, such as the tube of the infusion set, may consist of an outer and an inner material. The outer material may consist of a polyurethane (PU), such as Elastollan® 1185 A 10FC. The inner material may consist of a high density polyethylene (HDPE), such as SABIC® HDPE B5429 or a polypropylene (PP), such as Bormed™ SC820CF-11. The two-layer tube may be produced by a co-extrusion process, then cooled in a water bath, rolled up onto a roll and then cut to an appropriate length. The adhesion of the two layers may result from a chemical and/or physical process during the co-extrusion process. The two-layer tube does not include an adhesive layer between the two layers. By dispensing with an adhesive layer between the two layers, contamination by a substance absorbed in the adhesive layer into the liquid medicament to be dispensed may thereby be avoided.

In one embodiment of the supply line, such as the tube, the outside diameter of the outer material may be between 1.47 mm and 1.57 mm. The inner diameter of the outer material and the outer diameter of the inner material may be approximately 0.6 mm. The inside diameter of the inner material may be approximately between 0.26 mm and 0.34 mm.

In another embodiment of the supply line, such as the tube, the outer diameter of the outer material may be approximately between 1.47 mm and 1.57 mm. The inner diameter of the outer material and the outer diameter of the inner material may be approximately 0.8 mm. The inside diameter of the inner material may be approximately between 0.46 mm and 0.54 mm.

The wall thickness of the inner material may be reduced in such a way that less volume of the inner material may be used to manufacture the tube. Thus, less preservative, for example phenol or m-cresol, may be absorbed by the inner material of the tube and thus the shelf life of the liquid medicament to be dispensed through the tube may be increased.

The material for the outer material may have good tensile strength or good tear strength, hydrolysis resistance, low temperature flexibility and/or resistance to microorganisms.

The base part of the first and the second embodiment may have an uneven surface on the distal side. One or more of cams (or ridges) may be provided on the distal side of the base part. The plurality of cams may be arranged in a uniformly distributed manner on the distal side of the base part. Alternatively, the plurality of cams may be arranged in an irregularly distributed manner on the distal side of the base part. The cams may have an approximately pyramidal or conical shape. The cams may be connected to the adhesive layer, e.g., fused. The cams of the base part may be fused to the adhesive layer by ultrasonic welding such as by a sonotrode. When the base part is attached to the patient's skin, this arrangement may result in improved ventilation of the soft or the rigid cannula of the infusion set in the patient's skin, since air may circulate between the base part and the adhesive layer.

The base part of the first and the second embodiments may include a recess. The recess may be provided on the proximal side of the base part. A plurality of recesses may be provided. The recess or the plurality of recesses may be arranged on an edge of the base part. The base part may include a projection and a recess, such as a plurality of projections and a plurality of recesses. The projection and the recess, such as the plurality of projections and the plurality of recesses, may be provided on the proximal side of the base part. Furthermore, the projection and the recess, such as the plurality of projections and the plurality of recesses, may be arranged on the edge of the base part. The base part may have a projection and recess arrangement. The recess, such as the plurality of recesses, may be part of the projection and recess arrangement. The projection and recess arrangement may be provided on the proximal side of the base part. The projection and recess arrangement may be provided on the edge of the base part. The projection and recess arrangement may be formed continuously.

Furthermore, the base part may have an annular groove. The annular groove may be arranged on the distal side of the base part. The annular groove of the base part may be formed continuously.

The base part of the first and the second embodiment may be circular. Other configurations may be provided.

The base part of the first and second embodiment may be connected to the cap part for holding the infusion set by a patient or by an insertion device or puncture aid or may be connected, such as rotatably, to the connector part with a supply line for connection to an infusion device.

The base part of the first and second embodiments connected to the cap part may be attached to or removed from the patient's skin.

The connector part of the first and the second embodiment may be circular. The connector part may be configured in the shape of a cap. Furthermore, the connector part may be configured to be elastic. Other configurations may be provided.

The connector part may comprise a projection on the distal side. The projection may be provided on an edge of the connector part. The projection may be arranged on an inner surface of the cap-shaped connector part. The projection of the connector part may extend from the jacket inner surface at any angle to the axis of rotation, such as radially inward. Two projections may be provided on the connector part. The two projections may be arranged on the connector part offset from one another by 180°. Furthermore, a guide slot for guiding an edge of the base part may be provided on the connector part. The guide slot may be arranged proximally from the projection on the connector part. Two guide slots may be provided on the connector part. For instance, each guide slot may have a projection. A gripping element may be provided on an outer surface of the connector part. Furthermore, the gripping element may be provided offset by 90° to the guide slot and/or the projection or to the two guide slots and/or the two projections on the outer surface of the connector part. The gripping element may be arranged on the edge and on the outer surface of the connector part. The connector part may have two gripping elements. The gripping element may serve for better gripping of the connector part. The gripping element may be rib-shaped. The gripping element may be configured and/or arranged on the connector part in such a way that the patient may connect the connector part to the base part, e.g., snap it into place, and detach the connector part from the base part.

In order to releasably connect the connector part with the supply line to the base part, such as to snap it into place, the connector part may be placed on the base part. The piercing cannula arranged on the inside of the jacket of the connector part may penetrate through the septum of the base part in order to form a fluid connection between the connector part and the base part. The base part and the connector part may be rotatably connected to one another in order to administer the liquid medicament from the infusion device to the patient.

The connector part may be incorrectly or incompletely connected to the base part, and may be snapped into place faultily.

The projection of the connector part may be brought into engagement with the projection and recess arrangement in such a way that, upon relative rotation between the connector part and the base part, an acoustic and/or a tactile signal is generated to indicate that the connector part is incorrectly or incompletely connected to the base part connected. With relative rotation between the connector part and the base part, the projection of the connector part may slide over the projection and recess arrangement of the base part. An incorrect or incomplete connection, such as a faulty snap connection, may harbor the risk of an inadequate supply of medication, which is delivered to the patient from the connector part via the base part.

The connector part may be correctly or completely connected, such as snapped correctly, to the base part.

The projection of the connector part may be brought into engagement with the annular groove of the base part in such a way that the connector part may be rotated relative to the base part silently and/or without generating a tactile signal in order to indicate that the connector part is correctly or completely connected to the base part.

Furthermore, the edge of the base part may come into engagement with the guide slot provided on the connector part, such as with the two guide slots provided on the connector part.

The cap portion of the first and the second embodiment may be circular. The cap part may be configured in the shape of a cap. Furthermore, the cap part may be configured to be elastic. Other configurations may be provided.

The cap part may include a ratchet tooth or a locking tooth. The ratchet tooth may be arranged on an edge of the cap part. The ratchet tooth of the cap part may be arranged on the inside of the casing of the cap-shaped cap part. The ratchet tooth of the cap part may extend from the inner surface of the jacket at any angle to the axis of rotation, such as radially inward.

The ratchet tooth may be shaped in such a way that it fits into the recess, for instance into one of the several recesses of the base part. The ratchet tooth of the cap part may be brought into engagement, such as into a form or a locking engagement, with the recess, such as with a recess of the multiple recesses of the base part, in order to form a non-rotatable connection between the base part and the cap part.

In some implementations, two ratchet teeth may be provided on the cap part. The two ratchet teeth may be arranged on the cap part offset from one another by 180°. Furthermore, a guide groove for fastening the edge of the base part may be provided on the cap part. The guide groove may be arranged on the cap part distally from the ratchet tooth. Two guide grooves may be provided on the cap part. For instance, a ratchet tooth may be arranged on each guide groove. The cap part may include a holding element. The holding element may be arranged on a jacket outer surface of the cap part. The holding element may extend from the outer jacket surface of the cap part, for instance in the proximal direction. In some implementations, two holding elements arranged in parallel may be provided on the outer surface of the cap part. The holding element may be arranged approximately in axial alignment with the guide groove and/or the ratchet tooth. The holding element may be configured and/or arranged on the cap part in such a way that the patient may connect the cap part to the base part, such as snap it into place and detach the cap part from the base part. The cap part may include a handle part. The handle part may be arranged on the outer surface of the cap part and in the center of the cap part. The handle part may extend from the outer jacket surface of the cap part, such as in the proximal direction. In the first embodiment of the infusion set, the handle part may hold the rigid needle, where the rigid needle may extend from the inner surface of the cap part in the distal direction. The handle part may also serve to place the cap part connected to the base part, such as snapped onto it, into an insertion device or into a puncture aid. The soft or the stiff cannula of the infusion set may be placed directly into the skin by the insertion device or puncture aid and held in place with the adhesive layer. When the cap part is connected to the base part, such as snapped into place, the ratchet tooth of the cap part may engage in the recess of the projection and recess arrangement of the base part in order to prevent rotation. The engagement between the ratchet tooth of the cap part and the recess of the base part may prevent the cap part from rotating relative to the base part. The anti-twist device between the cap part and the base part enables the patient to better remove the protective film of the adhesive layer from the base part. For instance, a first anti-rotation lock may be formed between the handle part of the cap part and a receptacle of the insertion device or the puncture aid and a second anti-rotation lock may be formed between the ratchet tooth of the cap part and the recess of the base part, the two anti-rotation locks being able to help the patient better remove the protective film of the adhesive layer from the base part when the infusion set is inserted in the insertion device or in the puncture aid.

The cap part may further include a slot in the cap part between the handle part and the holding element. The slot may be arranged parallel to the holding element and/or to the guide groove of the cap part. The slot may be continuous or impervious. The slot may serve for better fastening of the cap part to the base part and for better detachment of the cap part from the base part.

BRIEF DESCRIPTION OF THE DRAWINGS

Implementations of the present disclosure are described below with reference to several figures. The features disclosed advantageously develop the implementations individually and in any combination of features.

DETAILED DESCRIPTION

Figure 1:
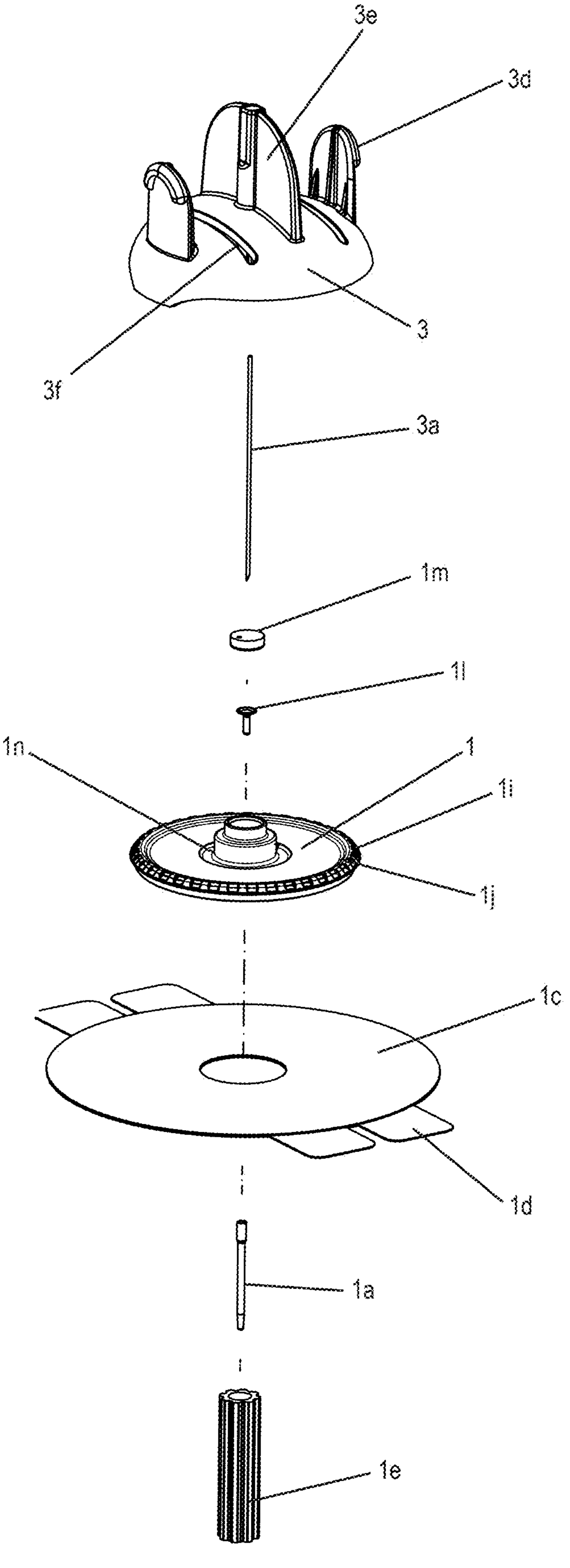
FIG. 1 shows an exploded view of a first embodiment of an infusion set according to implementations of the present disclosure, with a cap part and a base part of the infusion set being visible.

FIG. 1 shows an exploded view of an infusion set according to a first embodiment of the present disclosure, in which a cap part and a base part of the first embodiment of the infusion set are shown.

The infusion set comprises a circular and cap-shaped cap part (3) with a rigid needle (3*a*). The cap part (3) may be configured to be elastic or flexible. The rigid needle (3*a*) may be made of steel or an alternative material. The rigid needle (3*a*) may be firmly connected or affixed to the cap part (3). One or more holding elements (3*d*), e.g., two, and a handle part (3*e*) may be provided on an outer surface of the cap part (3). The holding element (3*d*) may be used to hold the infusion set and the handle part (3*e*) may be used to insert the infusion set into an insertion device or a puncture aid. Furthermore, one or more continuous slots (3*f*), e.g., two, may be provided in the cap part (3). A proximal end of the rigid needle (3) may be connected to the handle part (3*e*) of the cap part (3).

The infusion set may also comprise a circular base part (1), which may be configured to be flat. A protective element (1*e*) may be provided on the base part (1) to protect against puncture injuries caused by the rigid needle (3*a*). A plurality of projections (1*i*) and a plurality of recesses (1*j*) may be arranged on a proximal side and on the edge of the base part (1). The base part may further include a base cylinder (1*n*) which may be cylindrical. The base cylinder (1*n*) may be arranged on the proximal side of the base part and protrude in the proximal direction. A passage (FIG. 2; 1*o*) may be provided in the base cylinder. An "eyelet" (1*l*) may be inserted in the passage (FIG. 2; 1*o*) of the base cylinder (1*n*) in order to connect a soft cannula (1*a*) to the base part (1). The soft cannula (1*a*) may be made of a soft material. A cannula cylinder (1*f*) may protrude from the distal side of the base part (1) in the distal direction. The soft cannula (1*a*) may be fastened in the corresponding cannula cylinder (1*f*), for instance in a passage provided in the cannula cylinder (1*f*), and may protrude from the cannula cylinder (1*f*) in the distal direction in order to deliver the liquid medicament to the patient. The passage (FIG. 2; 1*o*) may be closed with a septum (1*m*), and the septum (1*m*) may be arranged at the proximal end of the "eyelet" (1*l*). Cams (or ridges) (FIG. 2; 1*h*) may be provided on a distal side of the base part. The cams (FIG. 2; 1*h*) may be fused to an adhesive layer (1*c*) of the base part (1) so that the adhesive layer may be connected to the base part (1). The adhesive layer (1*c*) may be used to attach the infusion set to the patient's skin. A distal side of the adhesive layer (1*c*) may be covered with a protective film (1*d*). Before applying the infusion set to the patient's skin, the patient takes the protective film (1*d*) off the adhesive layer (1*c*).

Figure 2:
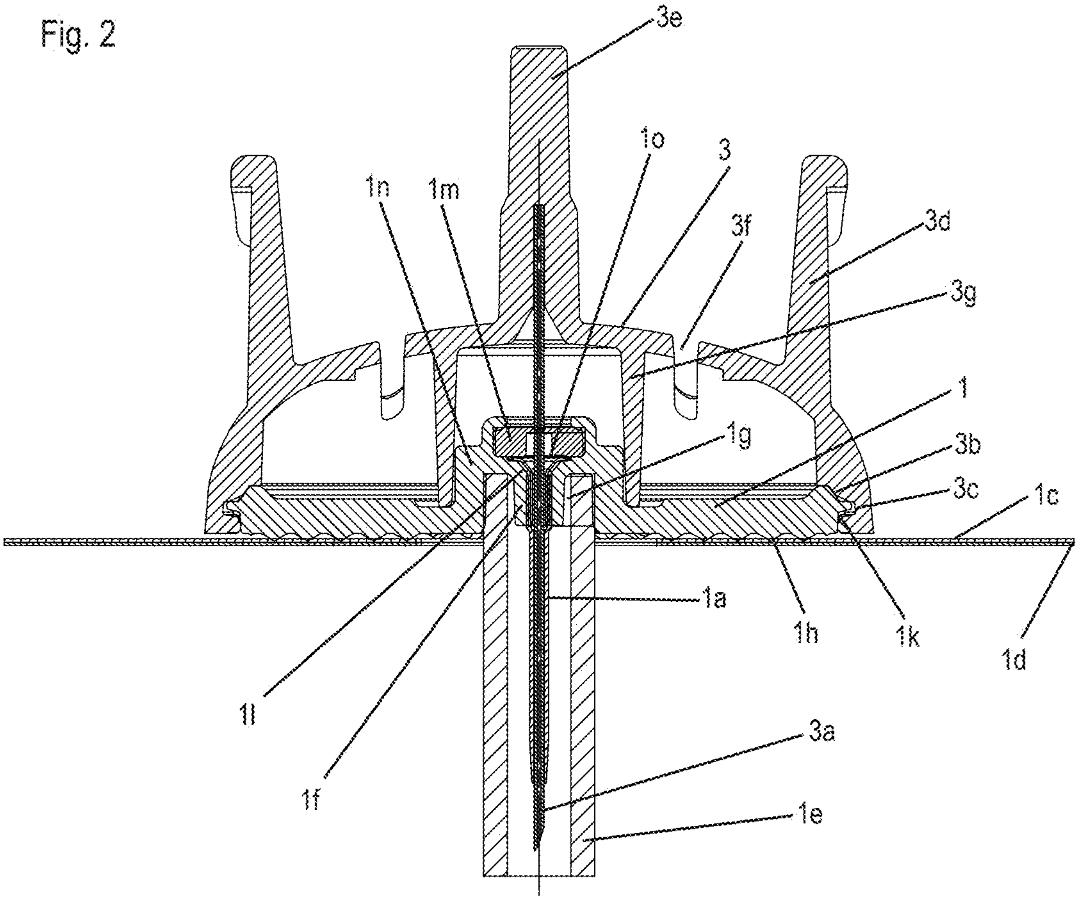
FIG. 2 shows a longitudinal sectional view of the infusion set according to FIG. 1, with the cap part being connected, e.g., snapped, to the base part.
Figure 7:
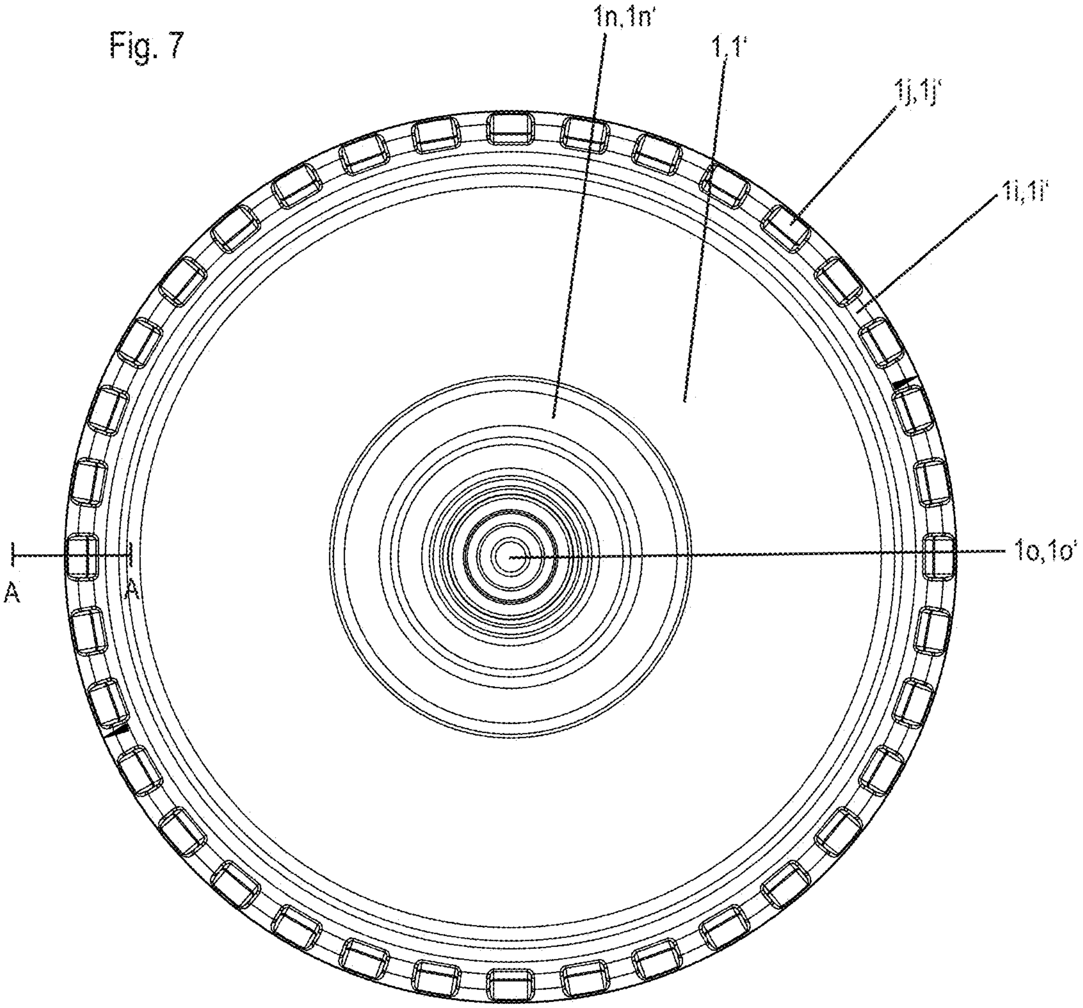
FIG. 7 shows a plan view of the base part of the first and the second embodiment of the infusion set.
Figure 8:
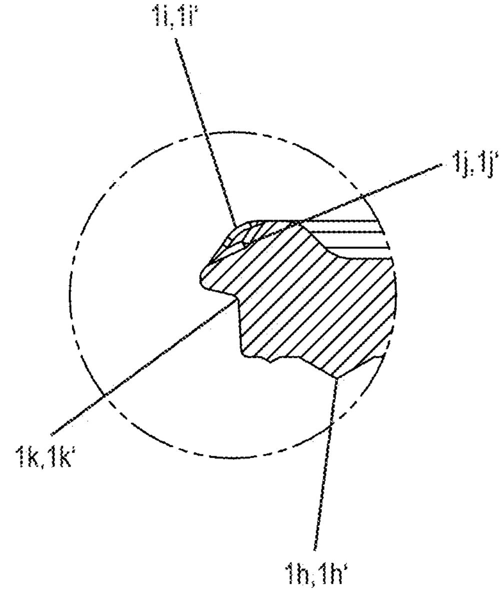
FIG. 8 shows a longitudinal sectional view of an edge of the base part of the infusion set along the section line A-A according to FIG. 7.
Figure 9:
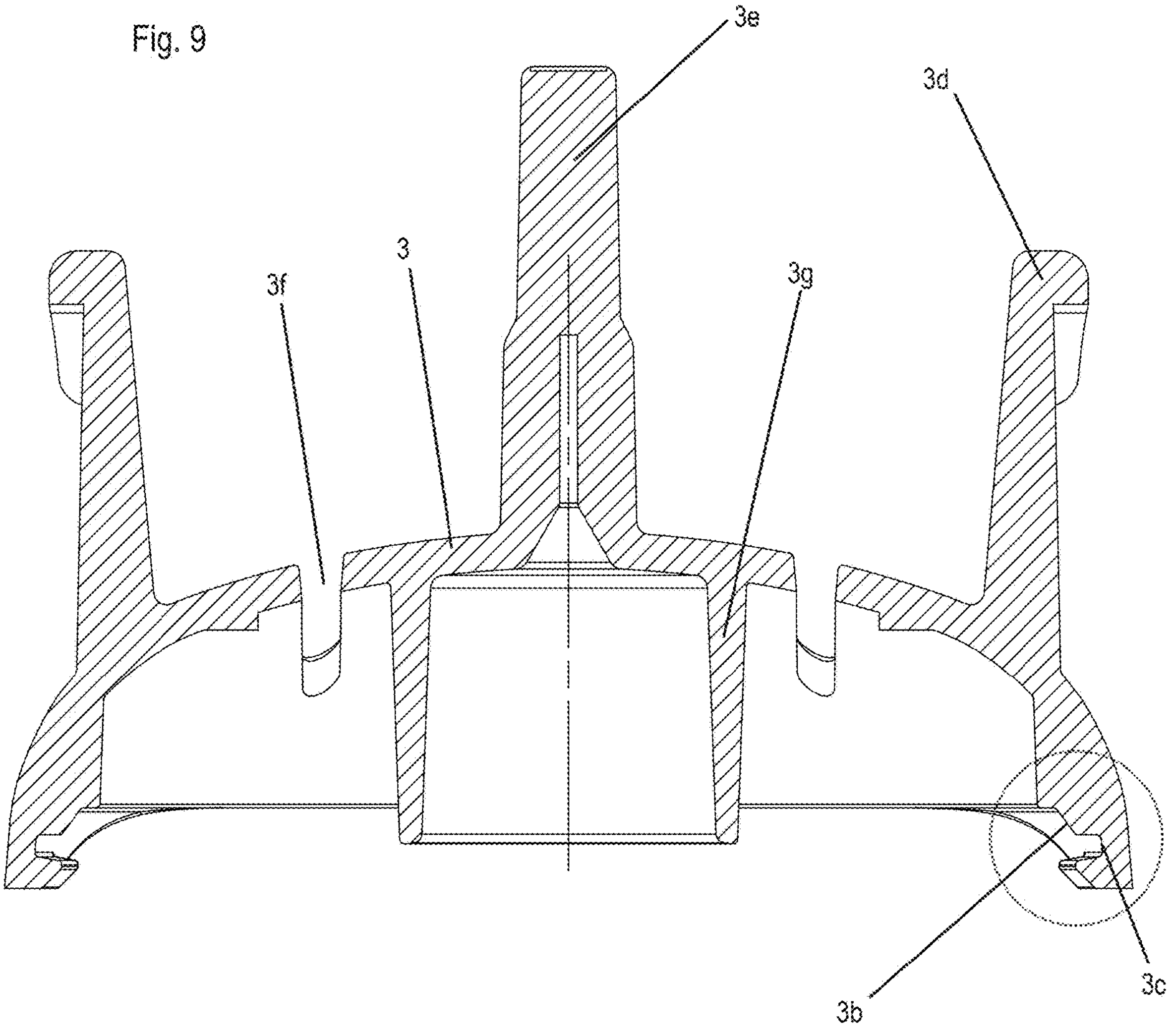
FIG. 9 shows a longitudinal sectional view of the cap part of the infusion set according to FIG. 1.
Figure 10:
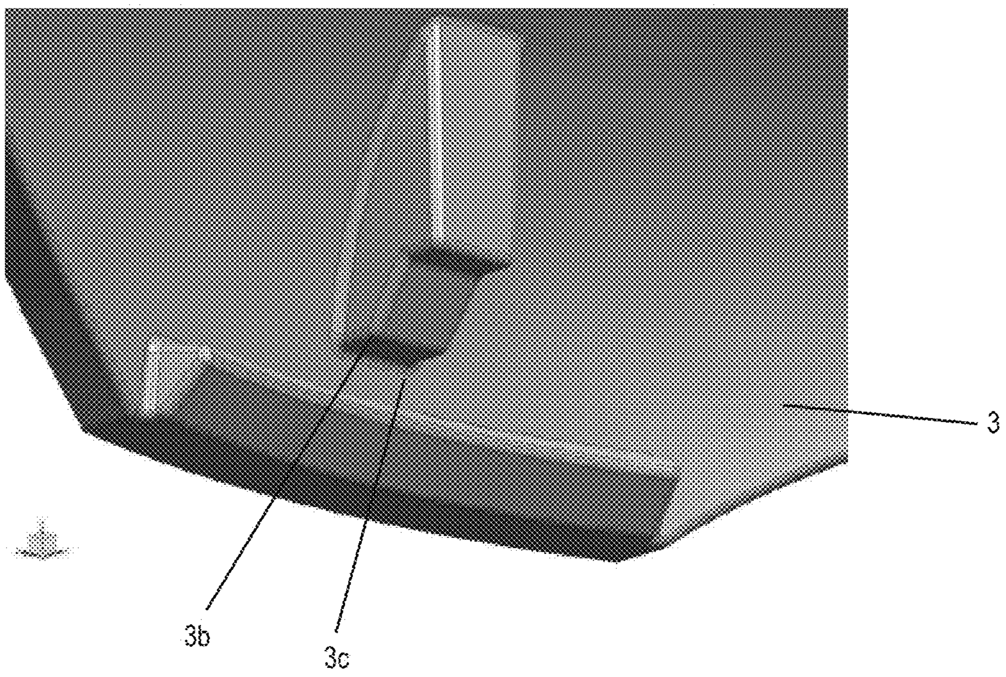
FIG. 10 is a perspective view of the section of the cap part identified in FIG. 9.

FIG. 2 shows a longitudinal sectional view of the infusion set according to FIG. 1, with the cap part (3) being connected to the base part (1), for instance by being snapped into place. The rigid needle (3*a*) of the cap part (3) may be received in the soft cannula (1*a*) of the base part (1) in such a way that a distal end of the rigid needle (3*a*) of the cap part (3) protrudes over a distal end of the soft cannula (1*a*) of the base part (1). The concentric arrangement of the soft cannula (1*a*) and the rigid needle (3*a*) may be used to guide the soft cannula (1*a*) when the soft cannula (1*a*) of the base part (1) is pierced into the patient's skin. The soft cannula (1*a*) may be positively connected to the "eyelet" (1*l*), for instance by being pressed and pressed into the passage (1*o*) of the base cylinder (1*n*). The protective element (1*e*) may be releasably pressed into an opening (1*g*) provided on a distal side of the base cylinder (1*n*) of the base part (1). The cap part (3) may be snapped onto a proximal side of the base part (1). The edge of the cap part (3) may include a guide groove (3*c*), which receives an edge of the base part (1). Furthermore, a ratchet tooth (3*b*) or a locking tooth may be provided on an inner surface of the cap part (3) and may protrude into a recess (1*j*) arranged on the distal side of the base part (1). When the cap part (3) is connected to the base part, a cap cylinder (3*g*) may be arranged concentrically to the base cylinder (1*n*) of the base part (1). As shown in FIG. 7 and in FIG. 8, the recess (1*j*) may be arranged on the edge of the base part (1). The recess (1*j*) may also form a part of a projection (1*i*) and recess arrangement (1*j*) of the base part (1). As shown in FIG. 9 and in FIG. 10, the ratchet tooth (3*b*) or locking tooth of the cap part (3) may protrude radially inward from the inside of the casing of the cap part (3). The ratchet tooth (3*b*) of the cap part (3) may be brought into an engagement, for instance, may form an engagement with the recess (1*j*) of the base part (1), in order to establish a non-rotatable connection between the base part (1) and the cap part (3). The non-rotatable connection between the cap part (3) and the base part (1) may enable the patient to remove the protective film (1*d*) of the adhesive layer (1*c*) more easily from the base part (1).

In order to attach the infusion set to the patient's skin, the patient may remove the protective element (1*e*) from the base part (1). The patient may then pull the protective film (1*d*) off the adhesive layer (1*c*). The cap part (3) snapped onto the base part (1) may be placed on the patient's skin. The soft cannula (1*a*) of the base part (1) with the rigid needle (3*a*) of the cap part received therein may penetrate through the skin and into the subcutaneous tissue. The cams (or ridges) (1*h*) of the base part (1) may space the base part (1) from the patient's skin and may enable air to circulate between the base part and the patient's skin. The cap part (3)

may then be removed from the base part (1) by the patient pretensioning the two holding elements (3*d*) inward, releasing the snap connection between the cap part (3) and the base part (1). The protective element (1*e*) may be placed over the rigid needle (3*a*) provided on the cap part (3) in order to protect the patient from puncture injuries. For instance, a holder provided on the inner surface of the cap part (3) may be provided for this purpose.

Figure 3:
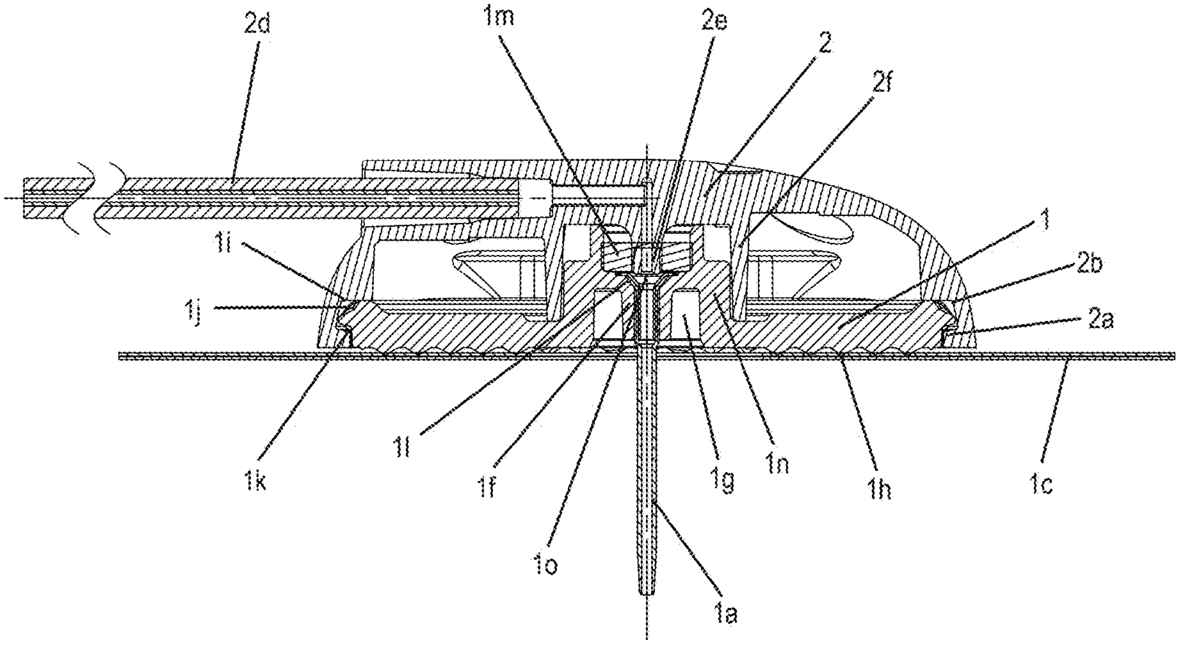
FIG. 3 shows a longitudinal sectional view of the infusion set according to FIG. 1, with a connector part being connected, e.g., snapped, to the base part.

Then, turning to FIG. 3, a connector part (2) with a tube (2*d*) may be attached to the base part (1). The tube (2*d*) may include an adapter for releasable attachment to an infusion device, such as an infusion pump. The tube (2*d*) of the connector part (2) may be connected to the adapter by using of an adhesive which hardens when exposed to UV light.

Figure 12:
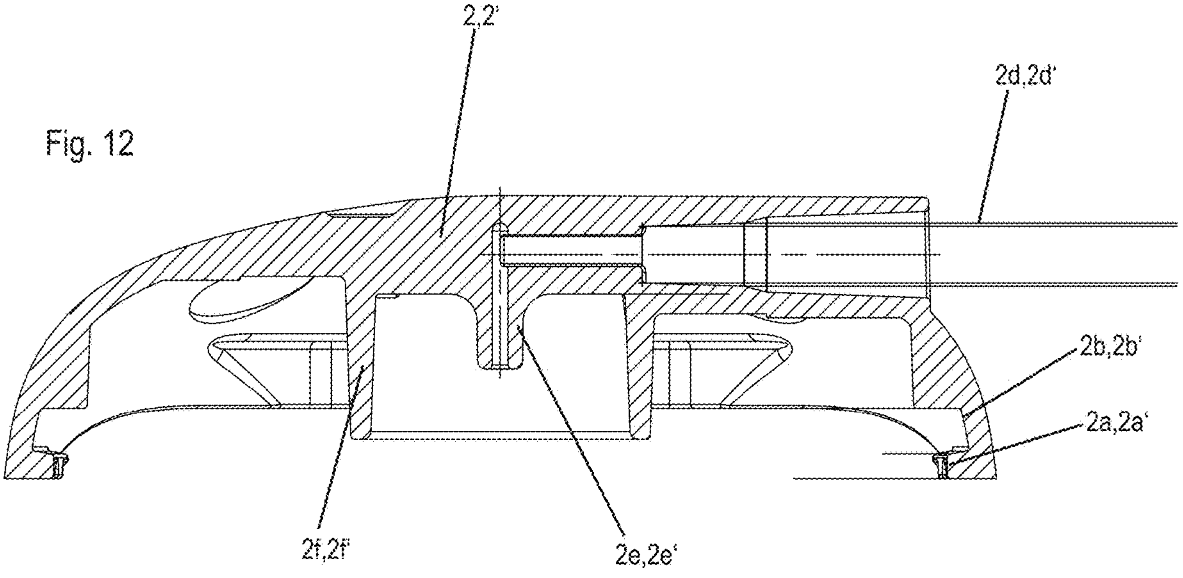
FIG. 12 is a longitudinal sectional view of the connector along the section line B-B according to FIG. 11.

FIG. 3 shows a longitudinal sectional view of the infusion set according to FIG. 1, a connector part (2) being connected, e.g., snapped, to the base part (1). The tube (2*d*) of the connector part (2) may be connected to the connector part (2) by an adhesive which cures by exposure to UV light. The tube (2*d*) may be in fluid connection with a piercing cannula (2*e*) arranged on an inner surface of the jacket. The tube (2*d*) may be arranged offset by 90° with respect to the piercing cannula (2*e*) in the connector part, as shown in FIG. 12. The piercing cannula (2*e*) of the connector part (2) may penetrate the septum (1*m*) provided on the base part (1) and may protrude into the "eyelet" (1*l*), for instance into the proximal part of the "eyelet" (1*l*) of the base part (1). A connector cylinder (2*f*) may be provided on the inner surface of the connector part (2) and may receive the base cylinder (1*n*) of the base part (1), which protrudes in the proximal direction. The connector cylinder (2*f*) may be in a guide engagement with the base cylinder (1*n*), for instance in a sliding engagement, with the connector part (2) being rotatable relative to the base part (1), for instance being rotatable through any desired rotational angle relative to one another. The drug to be dispensed may be administered into the patient's body by the infusion device via the connector part (2) and the base part (1).

With correct connection or complete snap action between the connector part (2) and the base part (1), as shown in FIG. 3, the edge of the base part (1) enters a guide slot (2*b*) provided on the connector part (2). Furthermore, a projection (2*a*) arranged on the inside of the casing of the connector part (2) protrudes into an annular groove (1*k*) provided on the base part (1). The projection (2*a*) of the connector part (2) may thus be in an engagement with the annular groove (1*k*) of the base part (1). With relative rotation between the connector part (2) and the base part (1), the projection (2*a*) of the connector part (2) slides silently and/or without a tactile signal generating in the annular groove (1*k*) of the base part (1).

In the event of an incorrect or incomplete connection, such as a faulty snap between the connector part (2) and the base part (1), the projection (2*a*) of the connector part (2) enters the projection (1*i*) and recess arrangement (1*j*) of the base part (1). The projection (2*a*) of the connector part (2) is in engagement with the projection (1*i*) and recess arrangement (1*j*) of the base part (1). With relative rotation between the connector part (2) and the base part (1), the projection (2*a*) of the connector part (2) slides over the projection (1*i*) and recess arrangement (1*j*) of the base part (1). In the event of a relative rotation between the connector part (2) and the base part (1), an acoustic and/or a tactile signal may be generated to indicate that the connector part (2) is not correctly or not completely connected to the base part (1), for instance is engaged incorrectly. An incorrect or incomplete connection, such as a faulty snap, harbors the risk of an inadequate supply of medication, which may be delivered to the patient from the connector part via the base part.

Figure 11:
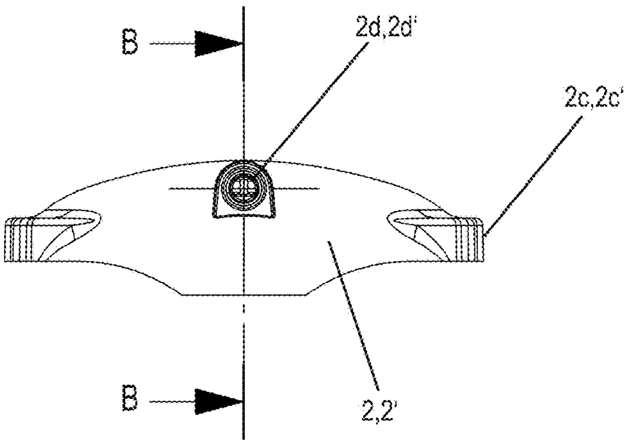
FIG. 11 is a side view of the connector of the first and second embodiment of the infusion set.
Figure 13:
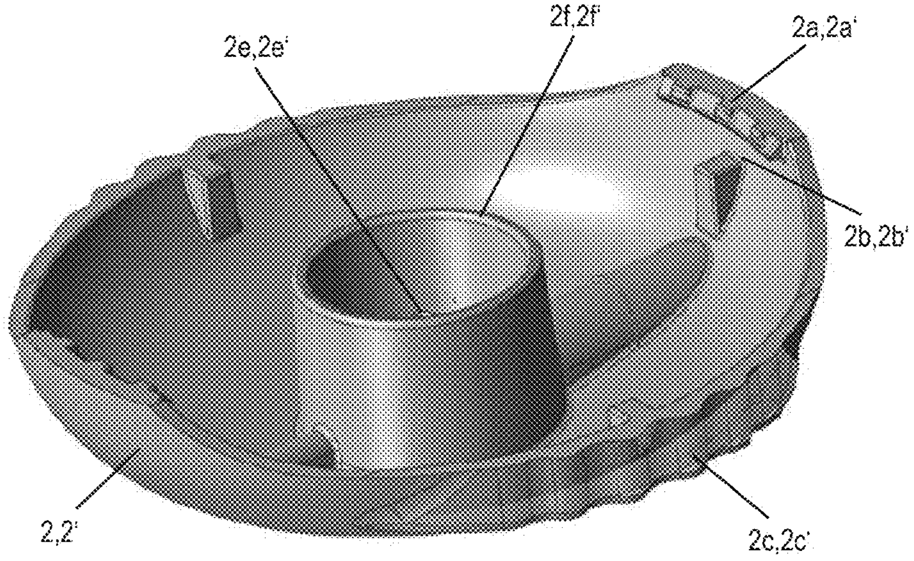
FIG. 13 a perspective view of the connector according to FIG. 12.

In order to detach the connector part (2) from the base part (1), the patient grips two gripping elements (2*c*) provided on the connector part (2) and presses inwards, as shown in FIG. 11 and FIG. 13. The snap connection between the connector part (2) and the base part (1) may thereby be released.

To remove the base part (1) from the patient's skin, the patient detaches the adhesive layer (1*c*) from the patient's skin and removes the base part (1) from the skin. Alternatively, the patient may connect the base part (1) to a cap part (3) which does not have a rigid needle (3*a*), and the patient may then be able to pull the cap part (3) connected to the base part (1) out of the patient's skin and dispose of the infusion set.

Figure 4:
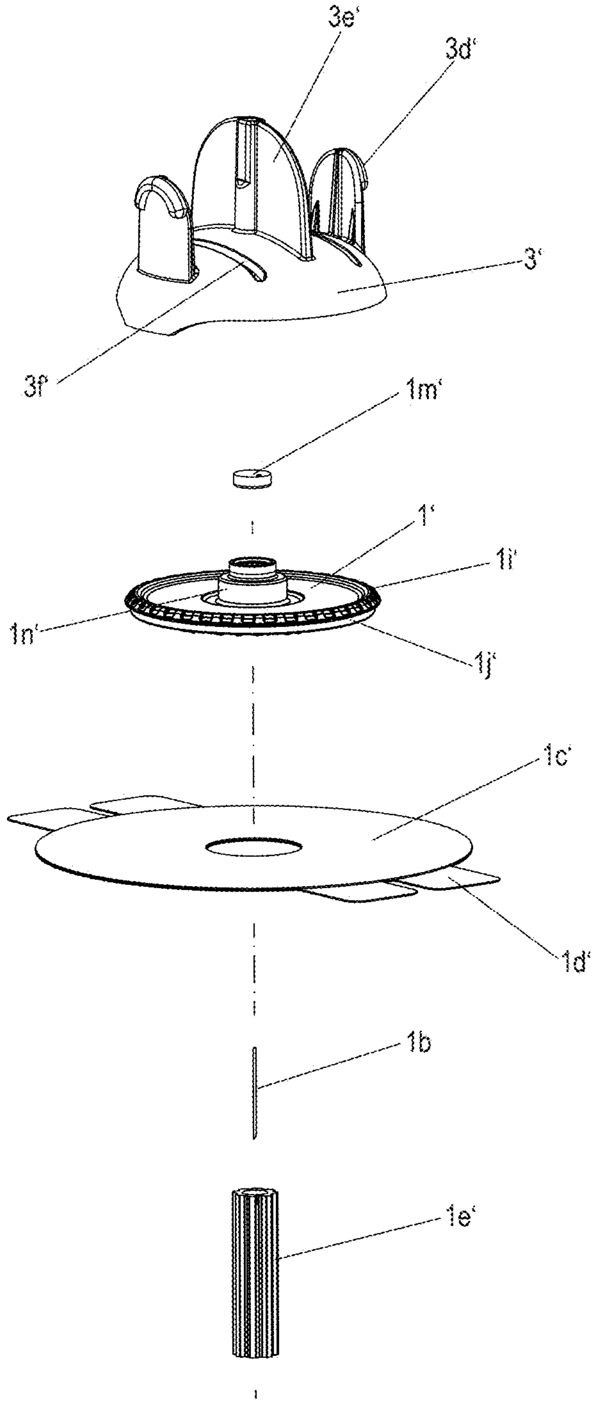
FIG. 4 shows an exploded view of a second embodiment of the infusion set according to implementations of the present disclosure, with a cap part and a base part of the infusion set being visible.

FIG. 4 illustrates an exploded view of a second embodiment of the infusion set according to implementations of the present disclosure, with a cap part (3') and a base part (1') of the infusion set being shown. Reference elements in the second embodiment labeled with an apostrophe ('), e.g., base part (1'), include similar configurations and functions as the same numbered reference elements discussed in the first embodiment without the apostrophe, e.g., base part (1), unless otherwise described, and those similarities are not repeated for purposes of clarity.

The infusion set may have a circular and cap-shaped cap part (3'). The cap part (3') may include one or more holding elements (3*d*'), e.g., two, and a handle part (3*e*'), which may be attached to an outer surface of the cap part (3'). Furthermore, one or more continuous slots (3*f*), e.g., two, may be provided in the cap part (3').

The infusion set may also include a circular base part (1'), which may be flat. In a passage (FIG. 5; 1*o*') of a base cylinder (1*n*') of the base part (1'), a rigid cannula (1*b*) may be attached. To fix the rigid cannula (1*b*) in the base part (1'), an adhesive may be applied between the rigid cannula (1*b*) and the cannula cylinder (1*f*'), such as an adhesive which hardens when exposed to UV light. A protective element (1*e*') may be provided on the base part (1') to protect against puncture injuries caused by the rigid cannula (1*b*). A plurality of projections (1*i*') and a plurality of recesses (1*j*') may be arranged on a proximal side and on the edge of the base part (1'). The passage (FIG. 5; 1*o*') may be closed with a septum (1*m*'), the septum (1*m*') being provided at a proximal end of the rigid cannula (1*b*). Cams (or ridges) (FIG. 5; 1*h*') may be arranged on a distal side of the base part. The cams (FIG. 5; 1*h*') may be fused with an adhesive layer (1*c*') of the base part (1') so that the adhesive layer may be attached to the base part (1'). The adhesive layer (1*c*') may be used to attach the infusion set to the patient's skin. A distal side of the adhesive layer (1*c*') may be covered with a protective film (1*d*'). Before attaching the infusion set to the patient's skin, the patient removes the protective film (1*d*') from the adhesive layer (1*c*').

Figure 5:
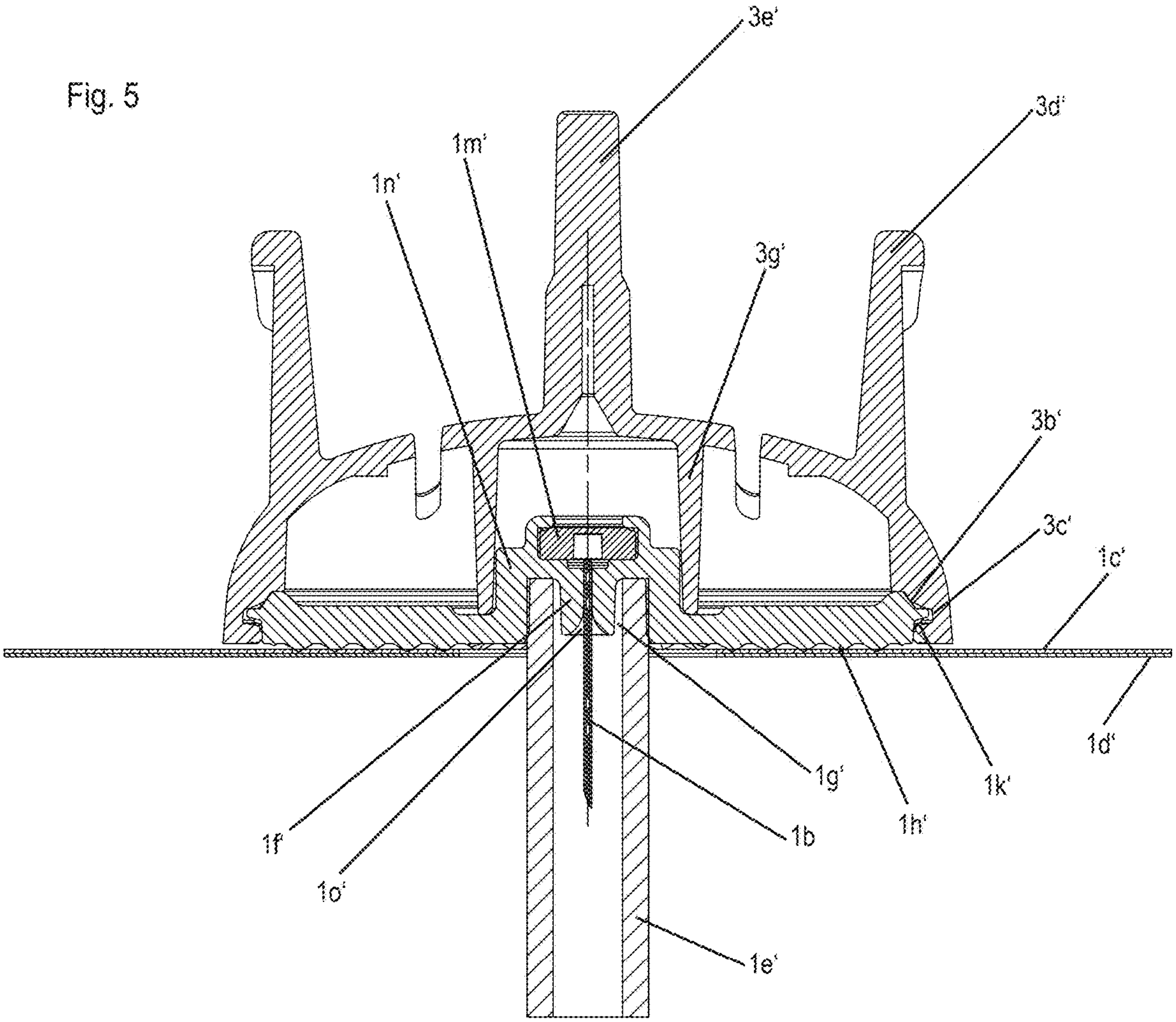
FIG. 5 shows a longitudinal sectional view of the infusion set according to FIG. 4, with a cap part being connected, e.g., snapped, to the base part.

FIG. 5 shows a longitudinal sectional view of the infusion set according to FIG. 4, the cap part (3') being connected, for instance snapped, to the base part (1'). The second embodiment of the infusion set differs from the first embodiment in that the cap part (3') does not have a rigid needle. Furthermore, instead of a soft cannula, the rigid cannula (1*b*) is attached to the base part (1'). The septum (1*m*') may close the proximal end of the rigid cannula (1*b*), which may be attached to the base cylinder (1*n*'). Due to the adhesive connection between the rigid cannula (1*b*) and the base cylinder (1*n*'), a connecting element, such as an "eyelet", may be unnecessary.

Figure 6:
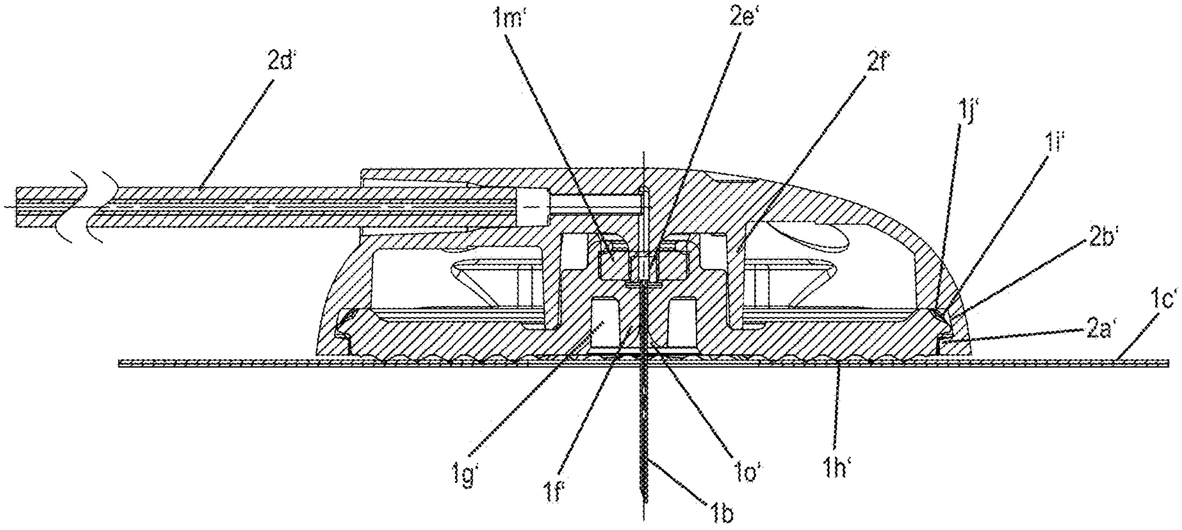
FIG. 6 shows a longitudinal sectional view of the infusion set according to FIG. 4, a connector part being connected, e.g., snapped, to the base part.

FIG. 6 shows a longitudinal sectional view of the infusion set according to FIG. 4, with a connector part (2') being connected, for instance snapped, to the base part (1'). The second embodiment of the infusion set differs from the first embodiment in that a piercing cannula (2*e*') provided on the connector part (2') penetrates through the septum (1*m*') of the base part (1') to form a fluid connection with the base part (1').

REFERENCE NUMBER

1; 1' base part
1*a* soft cannula
1*b* rigid cannula
1*c*; 1*c*' adhesive layer
1*d*; 1*d*' protective film
1*e*; 1*e*' protective element
1*f*; 1*f*' cannula cylinder
1*g*; 1*g*' opening
1*h*; 1*h*' cam (ridge)
1*i*; 1*i*' projection
1*j*; 1*j*' recess
1 k; 1*k*' annular groove
1*l* eyelet
1*m*; 1*m*' septum
1*n*; 1*n*' base cylinder
1*o*; 1*o*' passage
2, 2' connector part
2*a*; 2*a*' projection
2*b*; 2*b*' guide slot
2*c*; 2*c*' gripping element
2*d*; 2*d*' tube
2*e*; 2*e*' piercing cannula
2*f*; 2*f*' connector cylinder
3; 3' cap part
3*a* rigid needle
3*b*; 3*b*' ratchet tooth
3*c*; 3*c*' guide groove
3*d*; 3*d*' holding elements
3*e*; 3*e*' handle part
3*f*; 3*f*' slot
3*g*; 3*g*' cap cylinder

What is claimed is:

1. An infusion set, comprising:

a base part configured for attaching to skin of a patient, the base part comprising a proximal side and a distal side, wherein a cannula and an annular groove are provided on the distal side of the base part, the cannula configured for supplying a liquid medicament into the patient, and wherein a projection and recess arrangement is provided on the proximal side of the base part;

a connector part comprising a supply line configured for connecting to an infusion device, the connector part comprising a proximal and a distal side, wherein a projection is provided on the distal side of the connector part, wherein when the base part and the connector part are correctly or completely rotatably connected to one another in order to administer the liquid medicament from the infusion device to the patient, the projection of the connector part is in an engagement with the annular groove of the base part such that the projection slides in the annular groove and the connector part and the base part are rotatable relative to one another through any desired rotational angle noiselessly and/or without generating a tactile signal to thereby indicate that the connector part is correctly or completely connected to the base part, and wherein when rotatably connected and the connector part is incorrectly or incompletely connected with the base part, the projection of the connector part is in an engagement with the projection and recess arrangement of the base part such that relative rotation between the connector part and the base part causes the projection to slide over the projection and recess arrangement and generate an acoustic and/or a tactile signal to thereby indicate the connector part is incorrectly or incompletely connected with the base part.

2. The infusion set according to claim 1, wherein the base part is circular.

3. The infusion set according to claim 1, wherein the projection and recess arrangement is arranged on an edge of the base part.

4. The infusion set according to claim 1, wherein the connector part is cap-shaped and the projection is provided on an inner surface of the connector part.

5. The infusion set according to claim 1, wherein the connector part is circular.

6. The infusion set according to claim 1, wherein the projection is arranged on an edge of the connector part.

7. The infusion set according to claim 1, wherein the cannula is configured as a rigid cannula or as a soft cannula.

8. The infusion set according to claim 1, wherein the connector part comprises one or more guide slots for fastening to an edge of the base part.

9. An infusion set, comprising:

a base part configured for attaching to skin of a patient, the base part comprising a proximal side and a distal side, wherein a cannula and an annular groove are provided on the distal side of the base part, the cannula configured for supplying a liquid medicament into the patient, and wherein a projection and recess arrangement is provided on the proximal side of the base part;

a connector part comprising a supply line configured for connecting to an infusion device, the connector part comprising a proximal and a distal side, wherein a projection is provided on the distal side of the connector part, wherein the base part and the connector part are rotatably connected to one another in order to administer the liquid medicament from the infusion device to the patient, wherein when rotatably connected, the connector part and the base part are rotatable relative to one another through any desired rotational angle, and wherein when rotatably connected and the connector part is correctly or completely connected to the base part, the projection of the connector part is in an engagement with the annular groove of the base part such that the projection slides in the annular groove and the connector part rotates relative to the base part without generating noise and/or without generating a tactile signal to thereby indicate the connector part is correctly or completely connected to the base part, and wherein when rotatably connected and the connector part is incorrectly or incompletely connected with the base part, the projection of the connector part is in an engagement with the projection and recess arrangement of the base part such that the projection slides over the projection and recess arrangement and generates an acoustic and/or a tactile signal to thereby indicate the connector part is incorrectly or incompletely connected with the base part.

10. The infusion set according to claim 9, wherein the base part is circular.

11. The infusion set according to claim 9, wherein the projection and recess arrangement is arranged on an edge of the base part.

12. The infusion set according to claim 9, wherein the connector part is cap-shaped and the projection is provided on an inner surface of the connector part.

13. The infusion set according to claim 9, wherein the connector part is circular.

14. The infusion set according to claim 9, wherein the projection is arranged on an edge of the connector part.

15. The infusion set according to claim 9, wherein the cannula is configured as a rigid cannula or as a soft cannula.

16. The infusion set according to claim 9, wherein the connector part comprises one or more guide slots for fastening to an edge of the base part.

17. A method for assembling an infusion set, comprising the steps of:

providing a connector part comprising a supply line for connection to an infusion device, the connector part comprising a proximal side and a distal side, wherein a projection is provided on the distal side of the connector part;

providing a base part for attachment to skin of a patient, the base part comprising a proximal side and a distal side, wherein an annular groove and a cannula are provided on the distal side of the base part, the cannula for supplying a liquid medicament into the patient, and wherein a projection and recess arrangement is provided on the proximal side of the base part; and connecting the connector part to the base part in order to administer the liquid medicament from the infusion device to the patient, wherein when the connector part is connected to the base part, the connector part and the base part are rotatable relative to one another through any desired rotational angle, wherein when rotatably connected and the connector part is correctly or completely connected to the base part, the projection of the connector part is in an engagement with the annular groove of the base part such that relative rotation between the connector part and the base part results in the projection sliding in the annular groove without generating noise and/or without generating a tactile signal to thereby indicate the connector part is correctly or completely connected to the base part, and wherein when rotatably connected and the connector part is incorrectly or not completely connected to the base part, the projection of the connector part is in an engagement with the projection and recess arrangement of the base part such that the relative rotation between the connector part and the base part causes the projection to slide over the projection and recess arrangement and generate an acoustic and/or a tactile signal to thereby indicate the connector part is incorrectly or not completely connected to the base part.

18. The method of claim 17, wherein the connector part comprises one or more guide slots, and the one or more guide slots is in an engagement with an edge of the base part.

19. A method for assembling an infusion set, comprising the steps of:

providing a connector part comprising a supply line for connection to an infusion device, the connector part comprising a proximal and a distal side, wherein a projection is provided on the distal side of the connector part;

providing a base part for attachment to skin of a patient, the base part comprising a proximal side and a distal side, wherein an annular groove and a cannula are provided on the distal side of the base part, the cannula for supplying a liquid medicament into the patient, and wherein a projection and recess arrangement is provided on the proximal side of the base part; and rotatably connecting the connector part to the base part in order to administer the liquid medicament from the infusion device to the patient, wherein when rotatably connected and the connector part is correctly or completely connected to the base part, the projection of the connector part is in an engagement with the annular groove of the base part such that the connector part rotates relative to the base part through any desired rotational angle without generating noise and/or without generating a tactile signal to thereby indicate the connector part is correctly or completely connected to the base part, and wherein when rotatably connected and the connector part is incorrectly or not completely connected to the base part, the projection of the connector part is in an engagement with the projection and recess arrangement of the base part such that the connector part rotates relative to the base part and causes the projection to slide over the projection and recess arrangement and generate an acoustic and/or a tactile signal to thereby indicate the connector part is incorrectly or not completely connected to the base part.

20. The method of claim 19, wherein the connector part comprises one or more guide slots, and the one or more guide slots is in an engagement with an edge of the base part.

* * * * *